United States Patent [19]

Moody et al.

[11] 4,338,477
[45] Jul. 6, 1982

[54] REMOVAL OF CATALYST RESIDUES FROM A GAS

[75] Inventors: Keith Moody, Watsonia; Thomas Mole, Kew, both of Australia

[73] Assignees: ICI Australia Limited, Melbourne; Commonwealth Scientific and Industrial Research Organization, Campbell, both of Australia

[21] Appl. No.: 171,035

[22] Filed: Jul. 22, 1980

[30] Foreign Application Priority Data

Aug. 7, 1979 [AU] Australia ................................ PD9917

[51] Int. Cl.³ .................... C07C 2/02; C07C 7/144; C07C 7/12; B01D 53/02
[52] U.S. Cl. ...................................... 585/520; 55/74; 55/77; 55/98; 55/99; 585/521; 585/522; 585/523; 585/524; 585/818; 585/821
[58] Field of Search ......................... 55/74, 77, 98, 99; 585/520, 523, 524, 521, 522, 818, 821

[56] References Cited

U.S. PATENT DOCUMENTS

| | | | |
|---|---|---|---|
| 3,477,813 | 11/1969 | Fernald | 23/143 |
| 3,562,348 | 2/1971 | Jenkins | 260/677 |
| 3,589,863 | 6/1971 | Frevel et al. | 55/74 X |
| 3,782,076 | 1/1974 | Carr et al. | 55/74 |
| 3,992,282 | 11/1976 | Grosboll et al. | 55/98 X |
| 4,149,858 | 4/1979 | Noack et al. | 55/73 |

FOREIGN PATENT DOCUMENTS

| | | | |
|---|---|---|---|
| 633330 | 12/1961 | Canada | 585/523 |
| 985848 | 3/1976 | Canada | 585/521 |
| 2750428 | 6/1978 | Fed. Rep. of Germany | 55/99 |
| 1456897 | 9/1966 | France | 55/74 |
| 874577 | 8/1961 | United Kingdom | 585/523 |

*Primary Examiner*—John Doll
*Attorney, Agent, or Firm*—Cushman, Darby & Cushman

[57] ABSTRACT

The invention concerns a process for the removal of catalyst residues from a gas by contacting the gas with particulate mineral oxides. The process of the invention may be applied to the removal of coordination catalyst residues from α-olefins recycled from a polymerization reactor. The process is particularly useful in the removal of alkylaluminium halides and hydrogen halides, such as diethylaluminium chloride and hydrogen chloride, from α-olefins such as propylene. The process offers the advantages of being able to be operated under anhydrous conditions, and combining high efficiency in the removal of low levels of catalyst residues with a high capacity for the catalyst residues.

22 Claims, No Drawings

REMOVAL OF CATALYST RESIDUES FROM A GAS

This invention relates to the removal of catalyst residues from a gas and in particular to the use of particulate mineral oxides in the removal of catalyst residues from a gas.

α-Olefins and mixtures thereof may be polymerized to give a wide range of commercially useful polymers. The catalysts used to effect such polymerization reactions are conveniently prepared by combining one or more compounds of the transition elements of Groups IV-B, V-B and VI-B of the Periodic Table of Elements with one or more metallic reducing agents. Such catalysts are commonly referred to as coordination catalysts and certain of such catalysts are known as Ziegler and Ziegler-Natta catalysts.

The polymerization of α-olefins using coordination catalysts may be carried out employing a broad range of operating conditions. Polymerization temperatures may range from below 0° C. to above 250° C. and pressures may range from atmospheric pressure to pressures above 1 000 atmospheres. The polymerization reaction may be carried out either in a batch or continuous process in the gas phase or in the liquid phase optionally in the presence of an inert diluent or solvent. The catalyst may be present in supported or unsupported form as a dispersion, fixed-bed or fluidized-bed. In liquid phase reactions optionally carried out in the presence of an inert diluent or solvent, the catalyst may be present, unsupported, in solution.

That portion of the α-olefin which does not undergo polymerization and is discharged from the polymerization reactor may be disposed of simply by burning. However, for reasons of economy it is usual to recycle the α-olefin back into the polymerization reactor.

For the efficient polymerization of α-olefins using coordination catalysts it is necessary to use highly purified α-olefins and, therefore, it will be evident to those skilled in the art that the continuous recycling of the α-olefin not consumed in the polymerization reaction will lead to a progressive reduction in the purity of the α-olefin feed with deleterious effects on the efficiency of the polymerization process. As a result it is necessary to purify the recycled α-olefin before it is fed into the polymerization reactor.

The purification of the unreacted α-olefin is usually effected by fractionation to separate the desired α-olefin. Before carrying out this purification step it is desirable to remove any catalyst residues from the unreacted α-olefin discharged from the polymerization reactor. The removal of catalyst residues from the unreacted α-olefin reduces or eliminates the problems of corrosion that the catalyst residues might cause in the fractionation equipment and ensures that only the correct amount of fresh catalyst is fed into the polymerization reactor.

Prior to the present invention it has been common practice to remove catalyst residues from the recycled α-olefin stream by contacting that stream with steam or water to hydrolyze water sensitive catalysts. However, this process has the disadvantage that the wet recycle stream must be treated to remove the products of hydrolysis of the catalysts and then rigorously dried.

A novel, single-step process for the removal of catalyst residues from a gas has now been found.

Accordingly, the invention provides a process for the removal of catalyst residues from a gas which process comprises contacting said gas with particulate mineral oxide.

Suitable mineral oxides include those chosen from alumina, aluminosilicate, bauxite, silica, thoria, zirconia and mixtures thereof. Preferred mineral oxides for use in the process of the invention include alumina and aluminosilicate.

While the mineral oxide used in the process of the present invention is not narrowly critical, more preferred mineral oxides include certain types of alumina which combine the features of particularly effective adsorption of catalyst residues and acceptable flow rates through the adsorption material without unacceptable pressure drops. Examples of more preferred mineral oxides include α and γ aluminas of particle size in the range of from 0.25 inches (6.3 mm) to mesh size 20 (0.0331 inches or 0.85 mm). Particularly preferred mineral oxides include γ aluminas of particle size in the range from 6 to 16 mesh (3.35 mm to 1.18 mm).

Preferably the mineral oxide used in the process of the invention is substantially anhydrous. When the process of the present invention is used to remove catalyst residues from an α-olefin recycled from a polymerization reactor the use of an anhydrous mineral oxide is particularly advantageous as it reduces or removes the need to dry the recycle stream before it is fractionated to purify the α-olefin and/or before it is returned to the polymerization reactor.

The process of the present invention is particularly useful for the removal of catalyst residues from α-olefins as the process is effective in the removal of catalyst residues without the need to treat the α-olefin with steam or water and the catalyst residues may be essentially completely removed from the α-olefin with negligible loss of α-olefin through hydration or oligomerization reactions.

The process of the invention may be used in the removal of catalyst residues from a wide range of α-olefins including straight chain $C_2$ to $C_8$ α-olefins or branched chain $C_4$ to $C_8$ α-olefins or mixtures of $C_2$ to $C_8$ straight or branched chain α-olefins. Specific examples of suitable α-olefins include ethylene, propylene, but-1-ene, hex-1-ene and mixtures thereof.

The process of the invention is particularly effective in the removal of catalyst residues from the α-olefins ethylene, propylene or mixtures thereof.

The process of the present invention is particularly suitable for the removal from gases of residues from coordination catalysts used in the polymerization of α-olefins. Such coordination catalysts commonly comprise a combination of one or more compounds chosen from compounds of the transition elements of Groups IV-B, V-B, and VI-B of the Periodic Table of Elements with one or more metallic reducing agents or mixtures of such combinations. Typical examples of such coordination catalysts comprise a combination of one or more halo-vanadium, halo-titanium or halo-zirconium compounds with one or more metal alkyls, metal hydrides or alkali metals. Thus the α-olefin not consumed in the polymerization reaction, and discharged from the polymerization reactor, may contain catalyst residues comprising metal alkyls, alkylmetal halides, alkyl halides, hydrogen halides or mixtures thereof. If such catalyst residues are not removed from the unreacted α-olefin corrosion in the fractionation apparatus used to purify the α-olefin before it is recycled may cause significant problems resulting in the need to frequently replace equipment.

In the polymerization of the α-olefins ethylene, propylene and mixtures thereof the coordination catalysts used often comprise combinations of aluminum alkyls or alkylaluminum halides with titanium (III) and/or titanium (IV) halides. Such coordination catalysts are often called Ziegler or Ziegler-Natta catalysts. Typical components of such catalysts include alkylaluminum halides such as, for example, diethylaluminum iodide, diethylaluminum bromide and diethylaluminum chloride. Such components may give rise to catalyst residues comprising aluminum alkyls, alkylaluminum halides, alkyl halides, hydrogen halides or mixtures thereof.

Of the alkylaluminum halides used as components in the preparation of coordination catalysts, diethylaluminum chloride has found wide application in catalysts used in the polymerization of propylene. The process of the present invention has been found to be particularly effective in the removal of diethylaluminum chloride, hydrogen chloride or mixtures thereof from gases such as the α-olefin propylene.

Surprisingly, the process of the present invention combines the advantageous features of being able to efficiently remove catalyst residues from gases containing very low concentrations of such residues, and being able to remove large amounts of such residues from gases over prolonged periods without significant loss in efficiency. Moreover, the process may be used to efficiently remove low concentrations of coordination catalyst residues from α-olefins for prolonged periods, with the cumulative removal of large amounts of such residues, with the loss of only insignificant amounts of α-olefin through oligomerization reactions.

For example, a column of activated γ-alumina of particle size in the range from 8 to 14 mesh can reduce the diethylaluminum chloride concentration of propylene gas moving with a space velocity of 118 cubic meters per hour per ton of adsorbent ($m^3/hr/t$) from 41.0 parts per million (ppm) weight for weight (w/w) to 0.1 ppm w/w. This represents an adsorption efficiency of 99.7 percent. An adsorption efficiency of greater than 97 percent is possible even after the adsorption of at least 9 percent (w/w based on the alumina) of diethylaluminum chloride onto the alumina. Moreover, prolonged passage of propylene through an alumina column which had previously been loaded with over 8 percent (w/w based on the alumina) of diethylaluminum chloride resulted in the loss of less than 0.01 percent by weight of propylene through oligomer formation.

In the process of the present invention the gas containing catalyst residues may be contacted with the particulate mineral oxide in any suitable apparatus known in the art for the contacting of gases with solid particulate material. For example, the particulate mineral oxide may be in the form of a fixed bed or a fluidized bed. Simply passing the gas containing the catalyst residues through a column packed with the mineral oxide has been found to be an effective method for removing the catalyst residues from the gas.

The temperature and pressure at which the catalyst residues are removed from the gas according to the process of the present invention are not critical. Provided the medium to be contacted with the particulate mineral oxide is in the gaseous state any suitable combination of temperature and pressure may be used. For example, the temperature at which the process of the invention is carried out may range from −50° to 200° C. and the pressure may range from below atmospheric pressure to a pressure of 100 atmospheres or more. However, preferably the temperature is in the range from 0° to 100° C. and the pressure ranges from atmospheric pressure to 10 atmospheres.

From the foregoing description it will be evident to those skilled in the art that the process of the present invention is particularly applicable to operations involving the polymerization of α-olefins. Accordingly, in a further aspect the invention provides a process for the polymerization of α-olefins using a coordination catalyst which process comprises the removal of catalyst residues from the recycle gas by contacting said recycle gas with particulate mineral oxide.

The invention is now illustrated by, but in no way limited to the following examples.

EXAMPLES 1 TO 5

These examples demonstrate the effectiveness of different adsorbents in the removal of diethylaluminum chloride from a stream of nitrogen gas.

A steam of nitrogen gas containing diethylaluminum chloride (DEAC) was bubbled through a series of the three water traps and then was passed through a flow meter to establish both the flow rate and the volume of the gas. The concentration of aluminum in each trap was measured by atomic adsorption spectroscopy. No aluminum was detected in the third trap establishing that the first two traps were effectively removing the DEAC from the gas stream. From the volume of gas passed and the total aluminum concentration in the traps the DEAC content of the gas stream was calculated (DEAC in Gas, Before). Under identical flow conditions the same volume of gas was passed through a column of adsorbent and then through a series of three water traps. The concentration of aluminum in each trap was measured by atomic adsorption spectroscopy. Again no aluminum was detected in the third trap and the total aluminum concentration and volume of gas passed were used to calculate the DEAC content of gas stream exiting the adsorption column (DEAC in Gas, After).

The results are presented in Table 1 wherein Adsorbent No refers to the following adsorbents:

| Adsorbent No | Adsorbents | Column Dimensions Ratio, Length: Diameter |
|---|---|---|
| 1 | γ-Alumina 0.25" to 8 mesh | 2.6 |
| 2 | γ-Alumina 6 to 16 mesh | 10.4 |
| 3 | γ-Alumina 8 to 14 mesh | 4.1 |

TABLE 1

| Example No | Adsorbent No | Gas Temp (°C.) | Space Velocity ($m^3/hr/t$) | DEAC in Gas (ppm w/w) Before | DEAC in Gas (ppm w/w) After | Efficiency (%) |
|---|---|---|---|---|---|---|
| 1 | 1 | 16.5 | 206 | 39.3 | 9.7 | 75.4 |
| 2 | 2 | 12 | 236 | 16.5 | 2.2 | 86.7 |
| 3 | 2 | 12 | 486 | 94.8 | 7.8 | 91.8 |
| 4 | 2 | 13 | 216 | 281.8 | 13.5 | 95.2 |
| 5 | 3 | 22 | 204 | 31.2 | 1.3 | 95.8 |

EXAMPLES 6 TO 11

These Examples demonstrate the effectiveness of the process of the invention in the removal of diethylaluminum chloride and hydrogen chloride from a stream of nitrogen gas under a range of operating conditions.

A stream of nitrogen gas containing diethylaluminum chloride (DEAC) and hydrogen chloride was split into two separate streams. One stream (Control Stream) was bubbled through a series of three water traps and then passed through a flowmeter to establish both the gas flow rate and volume of gas. The other stream (Test Stream) was passed first through a column (length to diameter ratio of 4) of γ-alumina mesh size 8 to 14, which had previously been heated for a period of 12 hours at a temperature of 300° C., secondly through a series of three water traps and then through a flowmeter.

The DEAC concentrations in the gas stream before and after passage through the adsorbent were calculated from the Control Stream and Test Stream respectively from the total aluminum content of the traps and the volume of gas passed (see Example 1).

The total chloride content of the Control Stream water traps and the Test Stream water traps were determined by the use of an ion selective electrode. The chloride content of the Control Stream water traps and the volume of gas passed was used to calculate the total chloride concentration of the gas stream entering the adsorbent column and the chloride content of the Test Stream water traps and the volume of gas passed was used to calculate the total chloride concentration of the gas stream exiting the adsorbent column.

The results are presented in Table 2.

TABLE 2

| Example No | Gas Temp (°C.) | Space Velocity (m³/hr/t) | DEAC in Gas (ppm w/w) Before | DEAC in Gas (ppm w/w) After | Efficiency (%) | Total Cl in Gas (ppm w/w) Before | Total Cl in Gas (ppm w/w) After | Efficiency (%) |
|---|---|---|---|---|---|---|---|---|
| 6 | 20 | 194.2 | 40.8 | 1.2 | 97.1 | 32.0 | 2.5 | 92.1 |
| 7 | 40 | 246.5 | 69.4 | 1.7 | 97.6 | 28.4 | 0.5 | 98.1 |
| 8 | 40 | 204.6 | 35.4 | 0.4 | 98.9 | 13.3 | 0.3 | 98.0 |
| 9 | 20 | 192.2 | 53.3 | 2.3 | 95.7 | 20.5 | 0.5 | 97.5 |
| 10 | 60 | 229.5 | 84.7 | 2.3 | 97.3 | 31.2 | 0.7 | 97.8 |
| 11 | 60 | 198.8 | 61.5 | 1.7 | 97.3 | 26.6 | 0.4 | 98.6 |

EXAMPLES 12 TO 17

These Examples demonstrate the effectiveness of the process of the invention in the removal of diethylaluminum chloride and hydrogen chloride from a stream of propylene gas under a range of operating conditions.

The procedure described for Examples 6 to 11 was repeated substituting propylene gas for nitrogen gas and using, as adsorbent, a column (length to diameter ratio of 7.5) of γ-alumina of mesh size 8 to 14 which, prior to use, had been heated for a period of 12 hours at a temperature of 300° C.

The results are presented in Table 3.

TABLE 3

| Example No | Gas Temp (°C.) | Space Velocity (m³/hr/t) | DEAC in Gas (ppm w/w) Before | DEAC in Gas (ppm w/w) After | Efficiency (%) | Total Cl in Gas (ppm w/w) Before | Total Cl in Gas (ppm w/w) After | Efficiency (%) |
|---|---|---|---|---|---|---|---|---|
| 12 | 18.5 | 113 | 8.2 | 0.2 | 97.7 | 10.0 | 1.2 | 88.9 |
| 13 | 21 | 116 | 37.2 | 0.2 | 99.4 | 17.9 | 1.0 | 94.4 |
| 14 | 20 | 118 | 41.0 | 0.1 | 99.7 | 20.6 | 0.9 | 95.5 |
| 15 | 20 | 109 | 84.8 | 1.0 | 98.8 | 25.7 | 0.8 | 96.9 |
| 16 | 20 | 126 | 198 | 2.4 | 98.8 | 72 | 0.7 | 99.0 |
| 17 | 20 | 114 | 222 | 7.3 | 96.7 | 66.7 | 1.0 | 98.5 |

EXAMPLES 18 TO 23

These Examples demonstrate the continued effectiveness of the process of the invention in the removal of diethylaluminum chloride and hydrogen chloride from a stream of nitrogen gas after the adsorbent has adsorbed high loads of diethylaluminum chloride.

The procedure described for Examples 12 to 17 was repeated substituting nitrogen gas for propylene gas. Prior to the efficiency experiments reported in Examples 18, 19 and 20 the adsorbent was loaded with 1.64 percent (w/w based on the alumina) of diethylaluminum chloride by passing nitrogen gas containing diethylaluminum chloride through the adsorbent column for a prolonged period. Prior to the efficiency experiments reported in Examples 21, 22 and 23 the adsorbent was loaded with 8.92 percent (w/w based on the alumina) of diethylaluminum chloride by passing nitrogen gas containing diethylaluminum chloride through the adsorbent column for a prolonged period.

The results are presented in Table 4.

TABLE 4

| Example No | Gas Temp (°C.) | Space Velocity (m³/hr/t) | DEAC in Gas (ppm w/w) Before | DEAC in Gas (ppm w/w) After | Efficiency (%) | Total Cl in Gas (ppm w/w) Before | Total Cl in Gas (ppm w/w) After | Efficiency (%) |
|---|---|---|---|---|---|---|---|---|
| 18 | 19 | 118 | 42.9 | 0.9 | 98.0 | 38.0 | 0.8 | 98.0 |
| 19 | 17.5 | 122 | 20.2 | 0.1 | 99.6 | 16.5 | 0.5 | 97.0 |
| 20 | 17.5 | 118 | 2.0 | 0.05 | 97.6 | 11.6 | 0.4 | 96.3 |
| 21 | 20 | 112 | 72.9 | 0.7 | 99.1 | 29.0 | 0.5 | 98.4 |
| 22 | 20 | 125 | 56.1 | 1.1 | 98.0 | 26.7 | 0.5 | 98.1 |
| 23 | 20 | 108 | 98.4 | 1.8 | 98.2 | 32.4 | 0.5 | 98.4 |

EXAMPLES 24 TO 26

These Examples demonstrate the continued effectiveness of the process of the invention in the removal of diethylaluminum chloride and hydrogen chloride from a stream of propylene gas after the adsorbent has adsorbed high loads of diethylaluminum chloride.

The procedure described for Examples 18 to 23 was repeated substituting propylene gas for nitrogen gas. Prior to the efficiency experiments the adsorbent was loaded with 9.36 percent (w/w based on the alumina) of diethylaluminum chloride by passing nitrogen gas containing diethylaluminum chloride through the adsorbent column for a prolonged period.

The results are presented in Table 5.

TABLE 5

| Example No | Gas Temp (°C.) | Space Velocity (m³/hr/t) | DEAC in Gas (ppm w/w) Before | DEAC in Gas (ppm w/w) After | Efficiency (%) | Total Cl in Gas (ppm w/w) Before | Total Cl in Gas (ppm w/w) After | Efficiency (%) |
|---|---|---|---|---|---|---|---|---|
| 24 | 18 | 120 | 3.1 | 0.1 | 97.0 | 5.0 | 0.1 | 98.4 |
| 25 | 18 | 130 | 57.4 | 0.5 | 99.2 | 16.3 | 0.1 | 99.1 |

TABLE 5-continued

| Example No | Gas Temp (°C.) | Space Velocity (m³/hr/t) | DEAC in Gas (ppm w/w) Before | After | Efficiency (%) | Total Cl in Gas (ppm w/w) Before | After | Efficiency (%) |
|---|---|---|---|---|---|---|---|---|
| 26 | 18 | 131 | 69.7 | 0.7 | 99.0 | 22.6 | 0.2 | 99.3 |

EXAMPLE 27

This Example demonstrates that an insignificant amount of propylene gas is lost in oligomerization reactions during prolonged passage of the gas through an adsorbent heavily loaded with diethylaluminum chloride.

A 30 cm long column of diameter 4 cm packed with 377 g of 8–14 mesh γ-alumina, which had previously been heated for a period of 12 hours at a temperature of 300° C., was loaded with 8.36 percent (w/w based on the alumina) of diethylaluminum chloride by passing nitrogen gas containing diethylaluminum chloride through the adsorbent column for a prolonged period.

Propylene gas (43451 l; 68.859 kg), heated to a temperature of 50° C., was then passed through the column of adsorbent over a prolonged period at a space velocity of 116.5 m³/hr/t. After completion of the passage of propylene gas the alumina was treated with water to hydrolyze the diethylaluminum chloride and then was extracted three times with previously distilled hexane. The hexane extracts were filtered and the solvent removed to give 4.89 g of a pale yellow oil which was identified by proton magnetic resonance spectroscopy as propylene oligomer. The formation of 4.89 g of propylene oligomer from the 68.859 kg of propylene represents a loss of 0.0071 percent by weight of the propylene passed through the column.

We claim:

1. A process for the polymerization of α-olefins comprising
    (a) polymerizing α-olefins or mixtures thereof in the presence of a coordination catalyst,
    (b) isolating the α-olefin polymer produced,
    (c) recovering a recycle gas comprising unreacted α-olefin and catalyst residues and
    (d) removing said catalyst residues from said recycle gas by contacting said recycle gas with particulate mineral oxide.

2. A process according to claim 1 wherein the mineral oxide is alumina.

3. A process for the removal of catalyst residues from a gas which process comprises contacting with a particulate mineral oxide selected from the group consisting of alumina, aluminosilicate, bauxite, silica, thoria, zirconia and mixtures thereof a medium in the gaseous state, said medium comprising said gas and said catalyst residues.

4. A process according to claim 3 wherein said mineral oxide is alumina or alumino-silicate.

5. A process according to claim 4 wherein said mineral oxide is an α- or γ-alumina of particle size in the range of from 0.25 inches to mesh size 20.

6. A process according to claim 5 wherein said mineral oxide is a γ-alumina of particle size in the range of from 6 to 16 mesh.

7. A process according to claim 3 wherein said mineral oxide is anhydrous.

8. A process according to claim 3 wherein said gas comprises an α-olefin.

9. A process according to claim 8 wherein said α-olefin is chosen from $C_2$ to $C_8$ straight or branched chain α-olefins and mixtures thereof.

10. A process according to claim 9 wherein said α-olefin is chosen from ethylene, propylene, but-1-ene, hex-1-ene and mixtures thereof.

11. A process according to claim 10 wherein said α-olefin is chosen from ethylene and propylene.

12. A process according to claim 3 wherein said catalyst comprises a coordination catalyst.

13. A process according to claim 12 wherein said coordination catalyst comprises a combination of one or more compounds chosen from compounds of the transition elements of Groups IV-B, V-B, and VI-B of the Periodic Table of Elements with one or more metallic reducing agents or mixtures of said combinations.

14. A process according to claim 13 wherein said coordination catalyst comprises a combination of one or more halo-vanadium, halo-titanium or halo-zirconium compounds with one or more metal alkyls, metal hydrides or alkali metals or mixtures of said combinations.

15. A process according to claim 14 wherein said coordination catalyst comprises a combination of one or more titanium (III) halides or titanium (IV) halides with one or more aluminum alkyls or alkylaluminum halides or mixtures of said combinations.

16. A process according to claim 3 wherein said catalyst residues comprise metal alkyls, alkylmetal halides, alkyl halides, hydrogen halides or mixtures thereof.

17. A process according to claim 16 wherein said catalyst residues comprise, aluminum alkyls, alkylaluminum halides, alkyl halides, hydrogen halides or mixtures thereof.

18. A process according to claim 17 wherein said catalyst residues comprise diethylaluminum chloride, hydrogen chloride or mixtures thereof.

19. A process according to claim 3 wherein said particulate mineral oxide is in the form of a fixed bed or a fluidized bed.

20. A process for the removal of catalyst residues comprising diethylaluminum chloride, hydrogen chloride or mixtures thereof from a gas comprising propylene which process comprises contacting with particulate mineral oxide comprising γ-alumina of particle size in the range of from 8 to 14 mesh a medium in the gaseous state, said medium comprising said gas and said catalyst residues.

21. A process for the removal of catalyst residues from a gas comprising an α-olefin which process comprises contacting with a particulate mineral oxide selected from the group consisting of alumina, aluminosilicate, bauxite, silica, thoria, zirconia and mixtures thereof a medium in the gaseous state, said medium comprising said gas and said catalyst residues.

22. A process for the removal of catalyst residues from a gas comprising an α-olefin, said catalyst comprising a coordination catalyst, said process comprising contacting with a particulate mineral oxide selected from the group consisting of alumina, aluminosilicate, bauxite, silica, thoria, zirconia and mixtures thereof a medium in the gaseous state, said medium comprising said gas and said catalyst residues.

* * * * *